United States Patent [19]

Guinn

[11] Patent Number: 4,940,455
[45] Date of Patent: Jul. 10, 1990

[54] METHOD AND APPARATUS FOR SINGLE NEEDLE DIALYSIS

[75] Inventor: Perry W. Guinn, Idaho Falls, Id.
[73] Assignee: CD Medical, Inc., Miami Lakes, Fla.
[21] Appl. No.: 337,948
[22] Filed: Apr. 13, 1989
[51] Int. Cl.$^5$ ............................................. A61M 1/00
[52] U.S. Cl. ................................. 604/5; 128/DIG. 3
[58] Field of Search ................ 604/4, 5; 128/DIG. 3; 210/651, 416.1

[56] References Cited

U.S. PATENT DOCUMENTS

| | | | |
|---|---|---|---|
| 3,908,653 | 9/1975 | Kettering | 604/5 |
| 4,514,295 | 4/1985 | Mathieu et al. | 210/321.65 X |
| 4,614,590 | 9/1986 | Rath et al. | 604/5 X |
| 4,648,866 | 3/1987 | Malbrancq et al. | 210/651 X |
| 4,776,837 | 10/1988 | Kopp | 604/4 |

Primary Examiner—Robert A. Hafer
Assistant Examiner—Lynda M. Cofsky

[57] ABSTRACT

A dialysis apparatus includes a series blood circuit that extends from a single needle through a hemodialyzer and back to the needle. Extending from this circuit is a single ended arm that includes a pump and a blood accumulation chamber. The pump is cyclically operated in opposite directions (in cooperation with associated valves) to alternately withdraw blood from the patient to the chamber and to expel blood from the chamber back to the patient. During one of these operations, blood flows through the dialyzer. By hydraulically isolating the pump and expansion chamber from the series blood circuit, the apparatus avoids large pressure swings and the attendant ultrafiltration that can occur with other single needle systems.

7 Claims, 1 Drawing Sheet

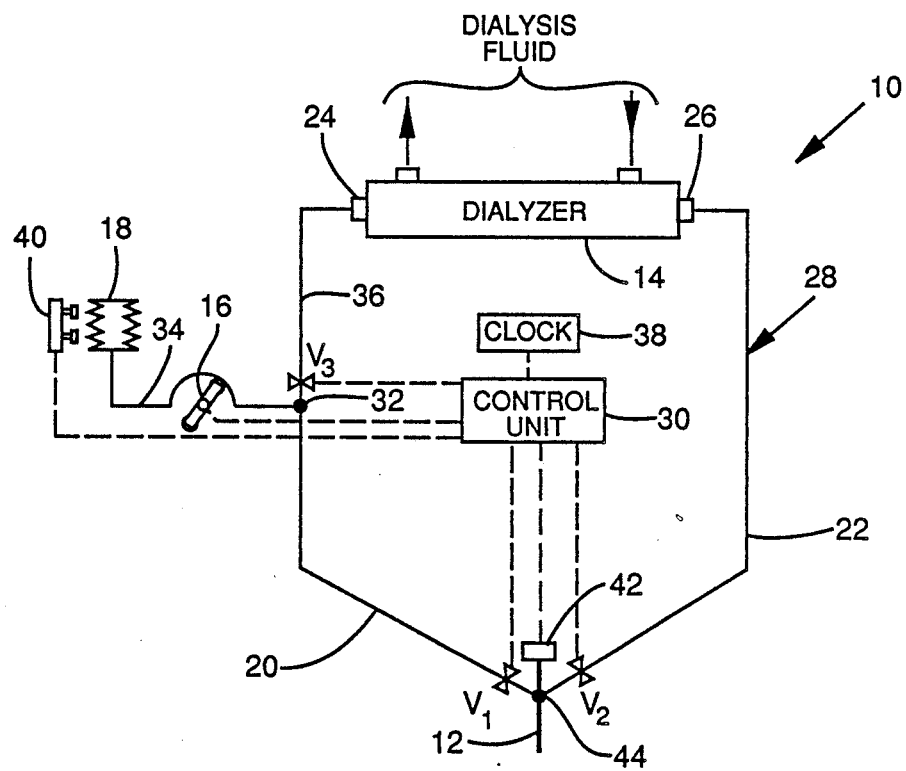

METHOD AND APPARATUS FOR SINGLE NEEDLE DIALYSIS

FIELD OF THE INVENTION

The present invention relates to dialysis machines, and more particularly relates to a method and apparatus for single needle dialysis.

BACKGROUND AND SUMMARY OF THE INVENTION

Single needle dialysis systems are known in the art and basically operate by cyclically withdrawing a volume of blood from a patient, passing it through a hemodialyzer, and returning it to the patient. The process then repeats, intermittently processing volumes of blood through the hemodialyzer. A single needle is used for both withdrawing and returning the blood—hence the name. (In two-needle systems, in contrast, one needle withdraws the blood and the second returns it, permitting continuous operation instead of cyclical.)

A principal problem with prior art single needle apparatuses has been the wide swings in the hemodialyzer blood pressure that are inherent in their designs. These pressure swings can cause intermittent massive ultrafiltration of the patient's blood. There is a need for a single needle dialysis device that overcomes this and other drawbacks of the prior art.

The present invention overcomes these pressure swings and the attendant ultrafiltration by use of an expansion chamber that extends from the blood circuit and is hydraulically isolated from the dialyzer by a blood pump. The invention also uses one pump (a reversible type) instead of the two conventionally used.

The foregoing and additional features and advantages of the present invention will be more readily apparent from the following detailed description, which proceeds with reference to the accompanying drawing.

BRIEF DESCRIPTION OF THE DRAWING

The drawing is a schematic illustration of a single needle dialysis system according to one embodiment of the present invention.

DETAILED DESCRIPTION

To provide a comprehensive disclosure without unduly lengthening this specification, applicant incorporates by reference the disclosures of U.S. Pat. Nos. 3,848,592, 3,938,909, 4,063,554, 3,908,653, 3,756,234, 3,811,800, 3,830,234, 3,985,134, 4,490,134 and 4,614,590 which show various single needle hemodialysis devices and teach certain fundamental concepts useful in the construction of a device according to the present invention.

Referring to the Figure, a single needle dialysis apparatus 10 according to one particular embodiment of the present invention basically includes a needle 12, a hemodialyzer 14, a reversible peristaltic pump 16 and an expansion chamber 18. To the needle 12 are connected an arterial blood line 20 and a venous blood line 22 which ultimately couple to the two ports 24, 26 of the hemodialyzer and form the basic blood circuit 28 of the device. Flow through each of lines 20, 22 is alternately blocked and opened by operation of valves $V_1$, $V_2$, respectively, under the control of a control unit 30.

Extending from a junction 32 in the arterial line 20 is a line 34 that couples to the expansion chamber 18 through the pump 16. A valve $V_3$ is interposed in a portion 36 of line 20 that extends from junction 32 to the arterial port 24 of the dialyzer 14. Under control of the control unit 30, pump 16 and valve $V_3$ cooperate to either provide blood from the patient to the expansion chamber 18 or to provide blood from the expansion chamber to the dialyzer. Pump 16 and valve $V_3$ also cooperate to hydraulically isolate pressure swings in the expansion chamber 18 and in line 34 from the dialyzer.

Operation of the apparatus proceeds in two phases. During the first phase, valves $V_2$ and $V_3$ are closed and the pump 16 is operated in a counter clockwise direction. In this direction, the pump acts to draw blood from the patient, through open valve $V_1$ and into the expansion chamber 18. During the second phase, valve $V_1$ is closed and the pump 16 is operated in a clockwise direction. In this direction, the pump acts to withdraw blood from the expansion chamber and pump it through the hemodialyzer and back into the patient through open valves $V_3$ and $V_2$. These operations are summarized in the following table:

| PHASE | EXPANSION CHAMBER | PUMP | $V_1$ | $V_2$ | $V_3$ | BLOOD FLOW THROUGH DIALYZER? |
|---|---|---|---|---|---|---|
| 1 | Filling | CCW | O | C | C | No |
| 2 | Emptying | CW | C | O | O | Yes | in which CCW is counter clockwise, CW is clockwise, C is closed and 0 is open.

Switching of the valves and pump direction to effect cyclical alternation of the phases is performed by the control unit 30. In one embodiment, an electronic clock 38 associated with the control unit causes the apparatus to switch between phases at a user-controlled periodic interval, such as once every two seconds. In another embodiment, switching is triggered by a physical sensor, such as a pressure or level sensor, somewhere in the system. For example, a level sensor 40 associated with the expansion chamber 18 may cause the control unit to switch from the first phase to the second when the level of accumulated blood in the chamber exceeds a first threshold, and switch from the second phase back to the first when the level of blood falls below a second threshold. In another embodiment, a pressure sensor 42 monitoring blood pressure at the junction 44 of the arterial and venous blood lines may cause the control unit to switch from the first phase to the second phase when that pressure rises above a first, lower threshold value, and switch from the second phase back to the first phase when that pressure falls below a second, higher threshold value.

Although omitted from the figure for clarity of presentation, a dialysis machine incorporating the present invention desirably includes drip chambers in both the arterial and the venous lines 36, 22. These chambers serve to remove bubbles from the blood before and after passage through the dialyzer, respectively.

A dialysis apparatus 10 according to the present invention can readily be modified to perform conventional double needle dialysis or any other therapy requiring continuous blood flow through the dialyzer. In such modification, the arterial and venous lines 20, 22 are provided with their own needles, valve $V_3$ is closed and the conduit 34 from the pump to the expansion chamber is routed instead to the arterial port of the dialyzer. The simplicity of the transformation permits a single apparatus to be quickly reconfigured to perform either type of therapy, a feature not provided by the prior art.

By employing a single peristaltic pump and expansion chamber that can be hydraulically isolated from both the hemodialyzer and the patient, the present invention avoids the large blood pressure swings at the hemodialyzer that occur with other single-needle hemodialysis devices. Further, because most existing single-needle hemodialysis devices utilize two peristaltic pumps rather than one, the present invention offers significant cost savings and improved reliability by eliminating one such pump.

Having described and illustrated the principles of my invention with reference to a preferred embodiment, it will be recognized that the invention can be modified in arrangement and detail without departing from such principles. For example, while the invention has been described as having the expansion chamber coupled to the arterial blood line, in other embodiments, the expansion chamber can be coupled to the venous blood line instead. Similarly, while the invention has been described as including only one expansion chamber, in other embodiments it may be desirable to include two or more. In one such embodiment, the second chamber can be used to permit continuous blood flow through the dialyzer if a double lumen needle is used.

In view of these and the wide variety of other embodiments to which the principles of my invention may be applied, it should be recognized that the illustrated embodiment is to be considered illustrative only and not as limiting the scope of the invention. Instead, I claim as my invention all such modifications as may come within the scope and spirit of the following claims and equivalents thereto.

I claim:

1. In a single needle dialysis apparatus that includes a blood circuit loop including tubing and extending from a single needle through a hemodialyzer and back to the single needle, an improvement comprising:
    blood accumulator means for accumulating a supply of blood; and
    pump means coupling the accumulator means to the blood circuit loop and operable in first and second directions for drawing blood from the single needle into the accumulator means when operated in the first direction and for pumping blood from the accumulator means through the dialyzer and back to the single needle when operated in the second direction;
    wherein said blood accumulator means and pump means form a single ended arm extending from said blood circuit loop.

2. The apparatus of claim 1 in which the blood circuit loop includes first and second blood lines coupling the needle to first and second ports of the hemodialyzer, respectively, and in which the apparatus further includes:
    a first valve for controllably occluding the first blood line's coupling to the needle;
    a second valve for controllably occluding the second blood line's coupling to the needle;
    a junction in the first blood line located between the first valve and the first port of the dialyzer from which the single ended arm extends;
    a third valve for controllably occluding a portion of the first blood line that extends from said junction to the first port of the hemodialyzer; and
    means operable alternately in two states, said means causing the second and third valves to open, the first valve to close, and the pump means to pump blood in a first direction through the single ended arm when in the first state; said means causing the second and third valves to close, the first valve to open, and the pump means to pump blood in a second direction opposite the first when in the second state.

3. The apparatus of claim 1 in which the blood circuit loop includes an arterial blood line and a venous blood line and in which the single ended arm extends from the arterial blood line.

4. The apparatus of claim 1 in which the blood accumulator means has a single port through which blood is supplied thereto and withdrawn therefrom.

5. The apparatus of claim 4 in which the pump means is a reversible peristaltic pump.

6. A method of single needle hemodialysis comprising the steps:
    providing only one pump through which blood flows;
    operating said pump in a first direction to withdraw a volume of blood through the needle to an accumulation chamber; and
    operating said pump in a second direction opposite the first to expel blood from the chamber through the needle;
    wherein one of said pump operations additionally serves to pass blood through a hemodialyzer.

7. In a method of single needle hemodialysis that includes passing blood through a series blood circuit that includes tubing and extends from a single needle through a hemodialyzer and back to the needle, an improvement comprising the steps:
    (a) withdrawing volume of blood from said series blood circuit and accumulating it in a container not included in said series circuit;
    (b) returning said volume of blood to the series circuit; and
    (c) cyclically alternating steps (a) and (b);
    wherein one of said withdrawing or returning steps additionally serves to pass blood through the hemodialyzer.

* * * * *